(12) United States Patent
Despiau et al.

(10) Patent No.: US 9,480,577 B2
(45) Date of Patent: Nov. 1, 2016

(54) RETAINING MECHANISM, IMPLANT, AND TOOL

(71) Applicant: Stryker Spine, Cestas (FR)

(72) Inventors: Jerome Despiau, Salles (FR); Cédric de Coninck, Rions (FR); Tan-Loc Pham, Pessac (FR)

(73) Assignee: Stryker European Holdings I, LLC, Kalamazoo, MI (US)

( * ) Notice: Subject to any disclaimer, the term of this patent is extended or adjusted under 35 U.S.C. 154(b) by 226 days.

(21) Appl. No.: 14/156,776

(22) Filed: Jan. 16, 2014

(65) Prior Publication Data
US 2014/0200671 A1    Jul. 17, 2014

Related U.S. Application Data (60) Provisional application No. 61/753,715, filed on Jan. 17, 2013.

(51) Int. Cl.
*A61F 2/44* (2006.01)
*A61B 17/84* (2006.01)
(Continued)

(52) U.S. Cl.
CPC ............. *A61F 2/447* (2013.01); *A61B 17/84* (2013.01); *A61F 2/30744* (2013.01); *A61F 2/4455* (2013.01); *A61F 2/4611* (2013.01); *A61B 17/8042* (2013.01); *A61F 2002/30136* (2013.01); *A61F 2002/30331* (2013.01); *A61F 2002/30439* (2013.01); *A61F 2002/30517* (2013.01); *A61F 2002/30563* (2013.01); *A61F 2002/30596* (2013.01); *A61F 2002/30598* (2013.01); *A61F 2002/30772* (2013.01); *A61F 2002/30777* (2013.01); *A61F 2002/30787* (2013.01); *A61F 2002/30836* (2013.01); *A61F 2002/4475* (2013.01); *A61F 2002/4627* (2013.01); *A61F 2310/00023* (2013.01)

(58) Field of Classification Search
CPC ...................................................... A61F 2/447
USPC ........................................ 606/283–285, 289
See application file for complete search history.

(56) References Cited

U.S. PATENT DOCUMENTS 6,206,882 B1 * 3/2001 Cohen ............... A61B 17/7059
606/283
6,629,998 B1    10/2003 Lin
(Continued)

FOREIGN PATENT DOCUMENTS

EP    1520545 A1    4/2005

OTHER PUBLICATIONS

Extended European Search Report for Application No. 14151371.3 dated Apr. 23. 2014.

*Primary Examiner* — David Bates
*Assistant Examiner* — Olivia C Chang
(74) *Attorney, Agent, or Firm* — Lerner, David, Littenberg, Krumholz & Mentlik, LLP (57) ABSTRACT

A retaining mechanism is disclosed, which comprises a plate including a first surface adapted to engage with an implant and a second opposing surface, the plate having mechanically-weakened areas, such that the plate is compressible from a first dimension to a second reduced dimension via the weakened areas, wherein the plate includes at least one ledge adapted to engage with a recess in the implant to prevent a fixation member inserted into the implant from backing out. A tool is also disclosed for compressing and inserting the retaining mechanism into engagement with the implant, as are respective methods of compression and insertion of the retaining mechanism into engagement with the implant.

13 Claims, 7 Drawing Sheets

(51) Int. Cl.
*A61F 2/30* (2006.01)
*A61F 2/46* (2006.01)
*A61B 17/80* (2006.01)

(56) References Cited

U.S. PATENT DOCUMENTS

2008/0287999 A1 11/2008 Markworth
2009/0224023 A1* 9/2009 Moskowitz ........ A61B 17/0642
227/181.1
2010/0286777 A1 11/2010 Errico et al.
2011/0029023 A1 2/2011 Tornier
2011/0301713 A1 12/2011 Theofilos
2011/0319893 A1* 12/2011 Stanaford .......... A61B 17/7059
606/70
2012/0232595 A1* 9/2012 Holschlag .......... A61B 17/8042
606/280
2012/0277870 A1* 11/2012 Wolters .................. A61F 2/447
623/17.16
2012/0289978 A1 11/2012 Jacob

* cited by examiner

RETAINING MECHANISM, IMPLANT, AND TOOL

CROSS-REFERENCE TO RELATED APPLICATIONS

The present application claims the benefit of the filing date of U.S. Provisional Patent Application No. 61/753,715, filed Jan. 17, 2013, the disclosure of which is hereby incorporated by reference herein.

BACKGROUND OF THE INVENTION

The present invention relates, in general, to retaining mechanisms for use with implants that, for example, prevent back-out of a fixation member(s) inserted into the implant.

In cases of spinal fusion, as an example, typically a spacer or other intervertebral implant is inserted into the patient to affect fusion across one or more levels of the spine. The spacer or other implant generally engages adjacent vertebral bodies to fuse and immobilize the site and mitigate patient discomfort. In some instances, screws are inserted into holes in the spacer or implant to retain the spacer or implant in place. Frequently, without a screw back-out mechanism, it is possible for such screws to come loose from the spacer or implant, causing the spacer or implant to become dislodged or unstable in the body. As such, various screw-retaining devices have been designed to prevent back-out of screws.

For instance, spacers currently offered in the industry include a back-out prevention mechanism in the form of a set screw(s) that, when rotated, covers a portion of multiple bone screws inserted through the spacer and into bone. Due to the set screw(s) covering the bone screws, the latter is prevented from backing out of connection with the spacer. When not rotated to cover the bone screws, the set screw(s) is of a geometry to allow insertion of the bone screws through holes in the spacer. With these types of constructions, however, it is possible for the set screw(s) to itself become dislodged after implantation, thereby affecting retaining of the bone screws. In other spacer constructions, bone screws are inserted into the spacer, and a circular locking cover is screwed into the spacer to cover the bone screws and prevent back-out.

Although mechanisms for preventing screw back-out have been developed, as described above, there remains a need for a comprehensive and effective system for preventing screw back-out when a bone screw(s) is inserted into a spacer or other implant device.

BRIEF SUMMARY OF THE INVENTION

A first aspect of the present invention provides a retaining mechanism comprising a plate with mechanically-weakened areas, such that the plate is compressible from a first dimension to a second reduced dimension via the weakened areas, wherein the plate includes at least one first portion adapted to engage with a second portion in an implant to at least partially block a fixation member inserted into the implant from backing out. In some cases, the weakened areas may include at least one cutout formed into the plate to allow the plate to compress to the second reduced dimension. Also, the plate may have opposed ledges extending outward from sides of the plate, the ledges being adapted to engage with corresponding recesses formed in the implant.

According to another aspect of the present invention, a system for preventing back-out of a fixation member is provided, the system comprising a retaining mechanism including a plate having a first surface and a second opposing surface, the plate containing mechanically-weakened areas adapted to permit compression of the plate from a first dimension to a second reduced dimension, wherein the plate includes at least one first portion. An implant may also be included with the system, the implant having opposed bone-contacting surfaces and comprising an opening adapted to receive the retaining mechanism, the implant having at least one second portion configured to receive the at least one first portion, such that the retaining mechanism at least partially blocks a fixation member inserted into the implant from backing out.

According to yet another aspect of the present invention, a system for preventing back-out of a fixation member is provided, the system comprising a retaining mechanism including a plate having a first surface and a second opposing surface, the plate being compressible from a first dimension to a second reduced dimension, wherein the plate includes at least one first portion, and an implant having opposed bone-contacting surfaces and comprising an opening adapted to receive the retaining mechanism, the implant having at least one second portion configured to receive the at least one first portion, such that the retaining mechanism at least partially blocks a fixation member inserted into the implant from backing out. In some embodiments of this aspect, the retaining mechanism includes opposed ledges extending outward from sides of the plate, the ledges being adapted to engage with corresponding recesses formed in the implant to prevent the retaining mechanism from disengaging with the implant.

BRIEF DESCRIPTION OF THE DRAWINGS

A more complete appreciation of the subject matter of the present invention(s) and of the various advantages thereof can be realized by reference to the following detailed description in which reference is made to the accompanying drawings in which:

FIGS. 4A-6 are exploded (FIG. 4A), side (FIGS. 4B, 5B), cross-sectional (FIGS. 4C, 5A, 5C), and top (FIG. 6) views of an instrument usable to compress the retaining mechanism of FIGS. 3A-C, and insert the same into engagement with, for example, the implant of FIGS. 2A-B.

DETAILED DESCRIPTION

In describing certain aspects of the present invention(s), specific terminology will be used for the sake of clarity. However, the invention(s) is not intended to be limited to any specific terms used herein, and it is to be understood that each specific term includes all technical equivalents, which operate in a similar manner to accomplish a similar purpose.

Figure 1A:
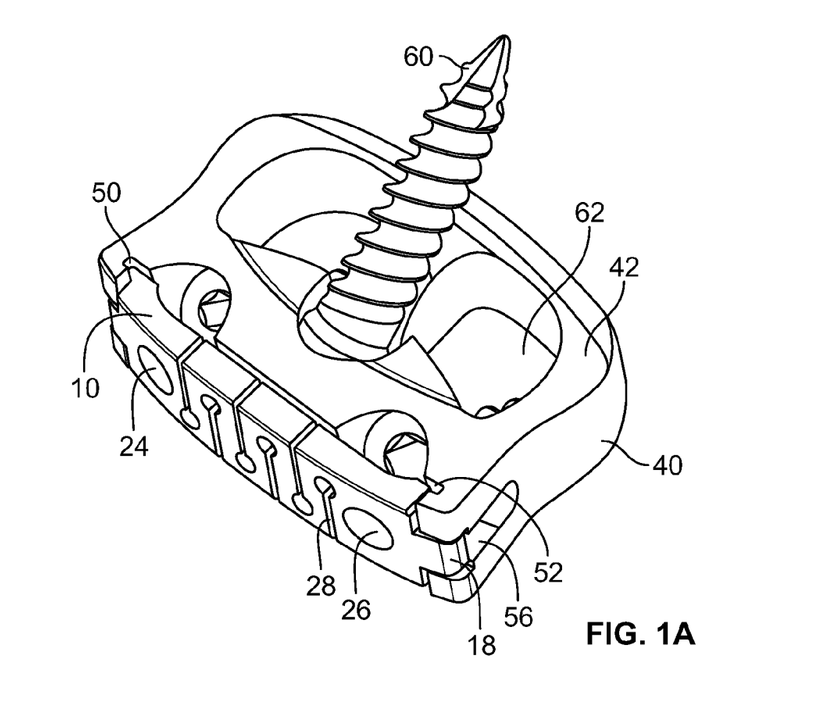
FIGS. 1A-B are perspective views of a retaining mechanism connected to an implant, in accordance with one embodiment of the present invention.
Figure 1B:
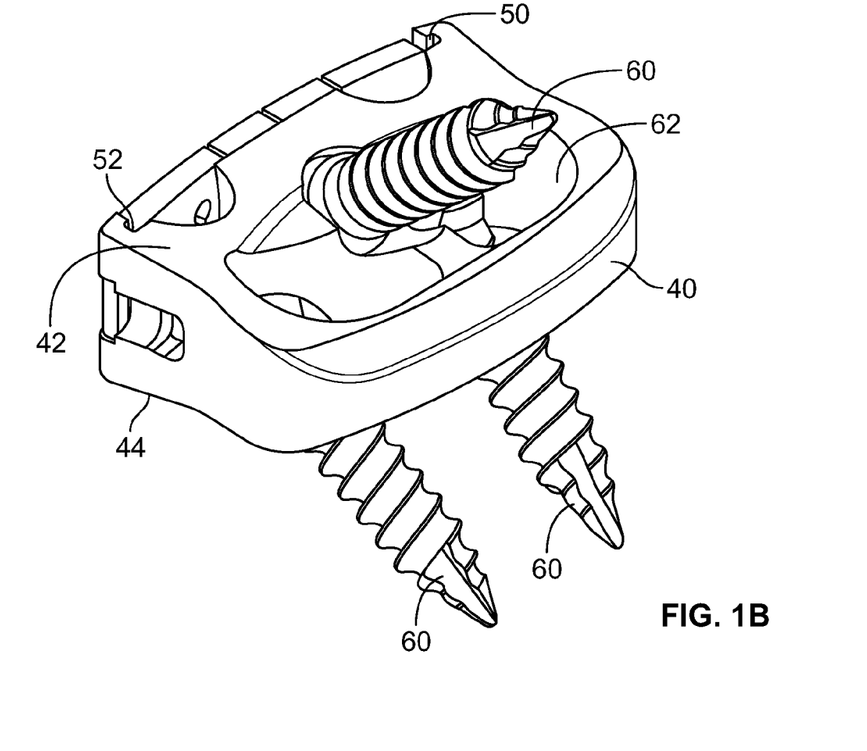

Referring to FIGS. 1A-B, a retaining mechanism 10 is shown, along with an implant 40 that may receive the retaining mechanism 10 to prevent fixation members 60 inserted into the implant 40 from backing out. Broadly, the retaining mechanism 10 may be in the form of a plate, which is compressible or otherwise deformable so as to engage with implant 40 to prevent fixation members 60 from backing out once secured therein. A tool 70 is also provided, as shown in FIGS. 4A-6, to compress or otherwise deform retaining mechanism 10 and insert such mechanism 60 into engagement with implant 40.

Figure 3A:
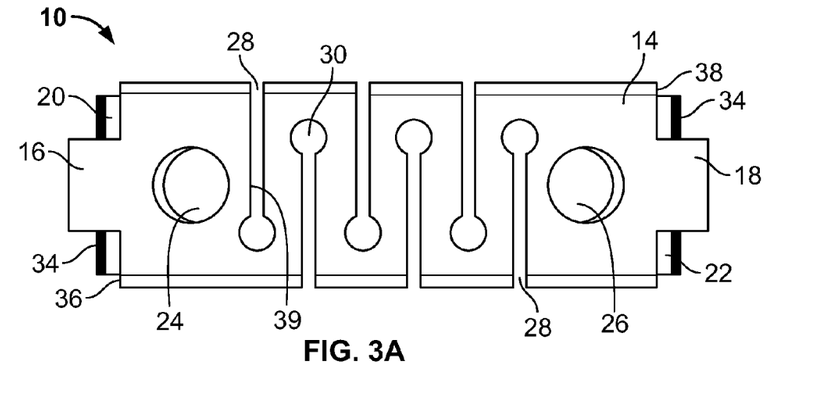
FIGS. 3A-C are various views of the retaining mechanism of FIG. 1 shown in compressed and uncompressed states.
Figure 3B:
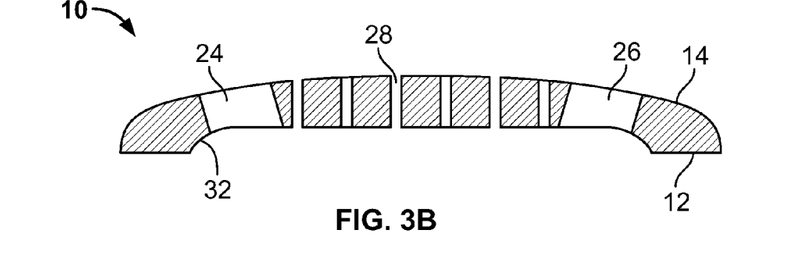
Figure 3C:
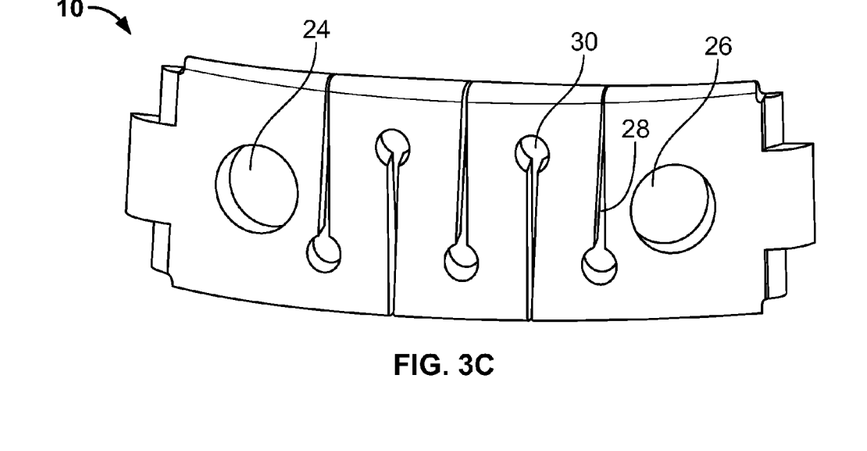

Retaining mechanism 10, as shown in detail in FIGS. 3A-C, includes inner and outer surfaces 12, 14 with at least one compressible or deformable area or cutout 28, and in some cases, multiple cutouts 28. The cutouts 28 may be adapted to allow compression or deformation of retaining mechanism 10 (FIG. 3C) and, in one embodiment, may extend completely through retaining mechanism 10 in a first direction (i.e., from inner surface 12 to outer surface 14), while extending only partially through retaining mechanism 10 in a second direction running perpendicular to the first direction. Retaining mechanism 10, in some instances, may include six (6) cutouts 28 that terminate in respective circular ends 30, although other amounts of cutouts 28 (e.g., besides six (6)) are contemplated, of course.

Referring to FIGS. 3A-3C, retaining mechanism 10 may be slightly concave-shaped 32 in one embodiment to conform to implant 40, and may include a set of holes 24, 26 for engaging with a portion of tool 70 (e.g., to compress or deform retaining mechanism 10). Arranged adjacent holes 24, 26 and extending from sides 36, 38 of retaining mechanism 10 may be one or more projections, and in a particular embodiment, multiple projections 16, 18. Projections 16, 18 may be configured to engage with slots 54, 56 situated in implant 40 (FIG. 2B) to stabilize retaining mechanism 10 upon engagement with implant 40. Also arranged on retaining mechanism 10 may be one or more ledges 20, 22 extending from sides 36, 38 of mechanism 10. Ledges 20, 22 may be sloped or tapered, and may include, in one embodiment, laser marks 34.

Figure 2A:
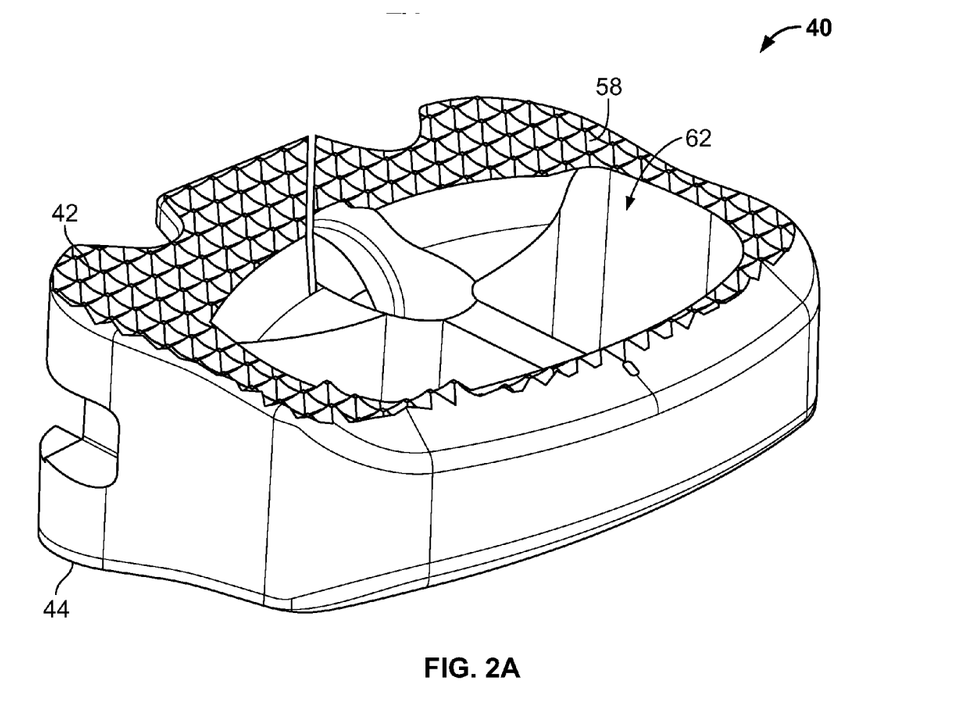
FIGS. 2A-B are perspective and back views, respectively, of one embodiment of an implant that is usable with the retaining mechanism of FIG. 1.
Figure 2B:
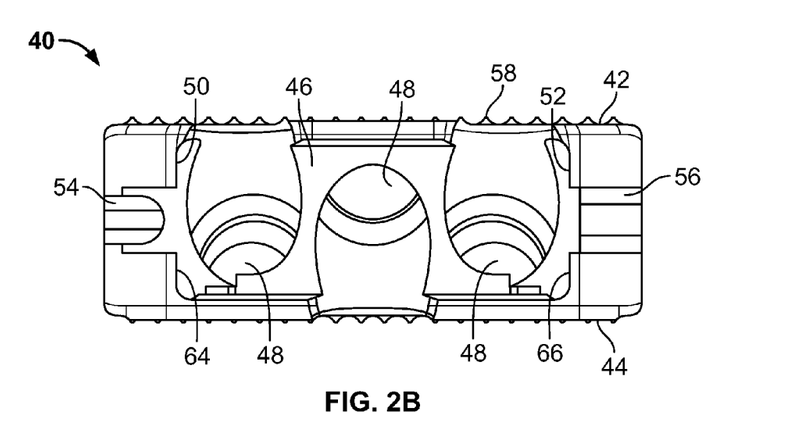

Referring now to FIGS. 2A-B, implant 40 may generally be in the form of a spacer having several common features, such as: (1) top and bottom bone-contacting surfaces 42, 44 with teeth or serrations 58; (2) an opening(s) 62 for receipt of bone in-growth material (e.g., osteoinductive and/or osteoconductive material, such as bone-graft material); (3) top and bottom bone-contacting surfaces 42, 44 that may be tapered to accommodate the natural lordosis of adjacent vertebral bodies; and (4) at least one hole 48 for receiving a fixation member 60, such as a bone screw. Apart from the aforementioned features, implant 40 may also have an opening or housing 46 for engaging with retaining mechanism 10, the housing 46 being defined by recesses 50, 52 formed in opposing walls 64, 66 of housing 46 (e.g., for engaging with ledges 20, 22). Implant 40 may also include a series of slots 54, 56 for receiving projections 16, 18 of retaining mechanism 10 to stabilize mechanism 10 once engaged with implant 40. Recesses 50, 52 may, in one embodiment, be formed on both sides of slots 54, 56 for engaging with ledges 20, 22 arranged on either side of projections 16, 18.

During use, a surgeon or other skilled practitioner (hereinafter "the user") may insert implant 40 into a patient, and attach fixation members 60, such as bone screws, to adjacent vertebral bodies to secure implant 40 to bone. With implant 40 secured, the user may then attach retaining mechanism 10 to implant 40 to prevent fixation members 60 from backing out (e.g., by covering a portion of fixation members 60 with retaining mechanism 10, as shown in FIGS. 1A-B). In particular, as reflected by the progression between FIGS. 3A and 3C, retaining mechanism 10 may be compressed or otherwise deformed from a first expanded dimension to a second reduced dimension in which the distance between ledges 20, 22 is decreased or altered. This decrease in distance between ledges 20, 22 may be affected by the compression or deformation of one or more cutouts 28. In short, walls 39 of cutouts 28 may be moved closer to one another about circular ends 30, thereby causing the distance between ledges 20, 22 to decrease. Alternatively, retaining mechanism may be compressed, deformed, or both to cause retaining mechanism to assume a configuration in which ledges 20, 22 may be inserted into recesses 50, 52. For instance, during compression of retaining mechanism 10, some degree of torsion or other such deformation may occur (intentionally or unintentionally), yet ledges 20, 22 may still be fitted within recesses 50, 52. Additionally, while cutouts 28 may allow elastic deformation of retaining mechanism 10 during such compression or deformation, once walls 39 come into contact with one another as shown in FIG. 3C, plastic deformation of mechanism 10 is prevented, and mechanism 10 is therefore able to spring back to its original shape, or another third shape (e.g., if restricted by a portion of implant 40 once engaged thereto).

Due to the aforementioned compression or deformation of retaining mechanism 10, ledges 20, 22 may be inserted within recesses 50, 52 so that an interference therebetween secures retaining mechanism 10 to implant 40 and prevents fixation members 60 from backing out. Indeed, the aforementioned compression or deformation of retaining mechanism 10 (and thus, for example, the decrease in distance between ledges 20, 22) may allow the user to insert ledges 20, 22 within recesses 50, 52, and upon return of retaining mechanism 10 to its decompressed/non-deformed state, ledges 20, 22 may engage with recesses 50, 52 and walls 64, 66 to prevent retaining mechanism 10 from disengaging with implant 40. At this point, certain portions of inner surface 12 of retaining mechanism may cover one or more fixation members 60 so that such fixation members 60 cannot come loose and/or back out of holes 48 (e.g., potentially causing soft-tissue irritation, or dislodging of implant 40 within the body, etc.) As such, retaining mechanism 10 may reliably ensure that implant 40 and fixation members 60 remain in place once implanted within a patient.

Referring now to FIGS. 4A-6, in one embodiment a tool 70 may be provided for engaging retaining mechanism 10 with implant 40. Tool 70 may include a shaft 72 with proximal and distal ends 74, 76, the proximal end 74 having a handle 86, and the distal end 76 having a set of L-shaped arms 78, 80. As shown in FIG. 4C, handle 86 of tool 70 may also include an opening 100 for receiving an inner shaft 88 therethrough. Referring again to FIG. 4A, a link 92 may also be attached to inner shaft 88 via a dowel 96, and the combination of inner shaft 88 and link 92 may be attached to a lever 90 situated proximate handle 86 (e.g., also via a dowel 96). Lastly, an adjustment nut 94 may be threaded over shaft 72 and handle 86 to connect such components together. Arms 78, 80, in one embodiment, may also include a set of posts 82, 84 for engaging with holes 24, 26 of retaining mechanism 10.

Figure 4A:
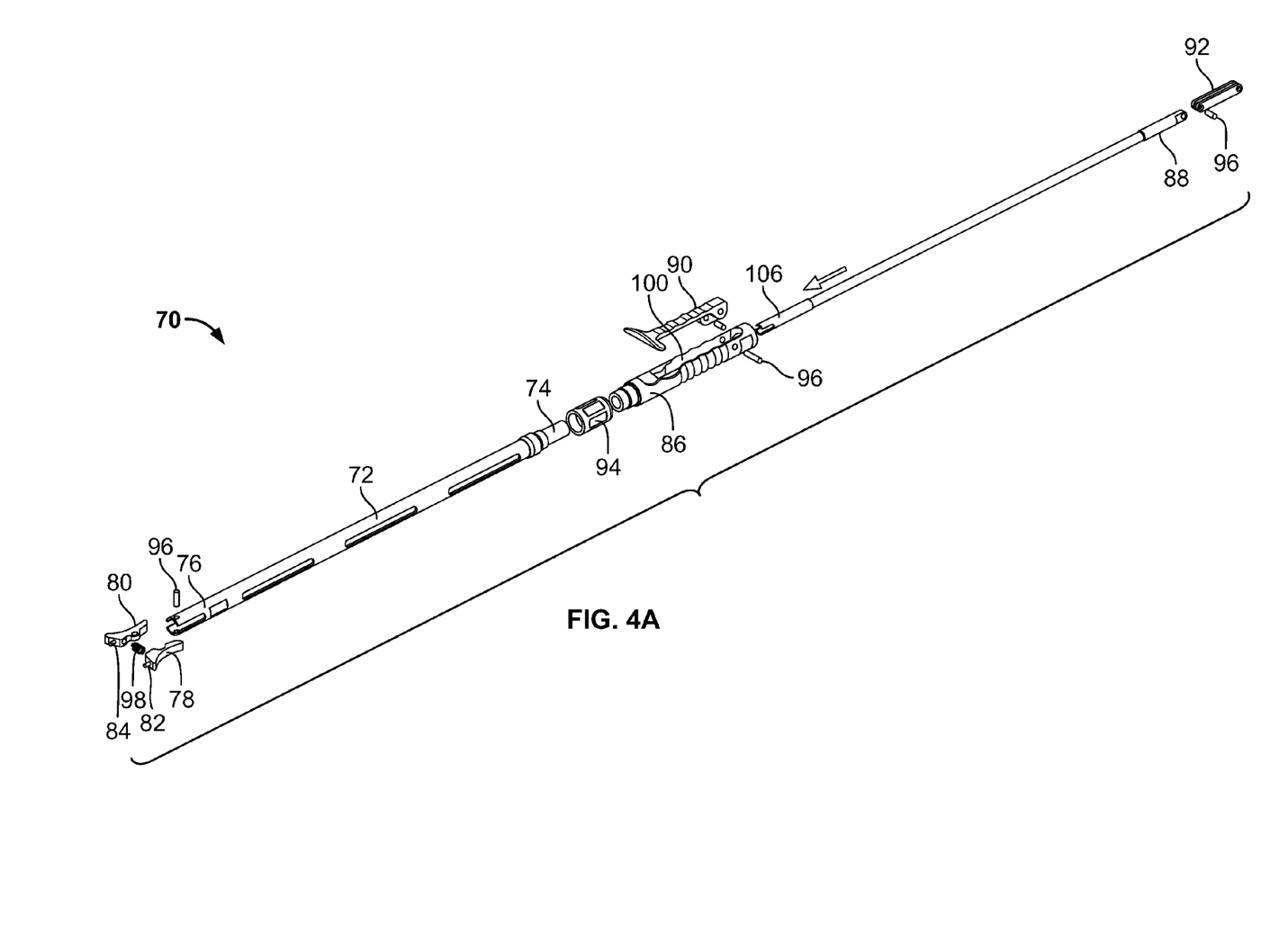
Figure 4B:
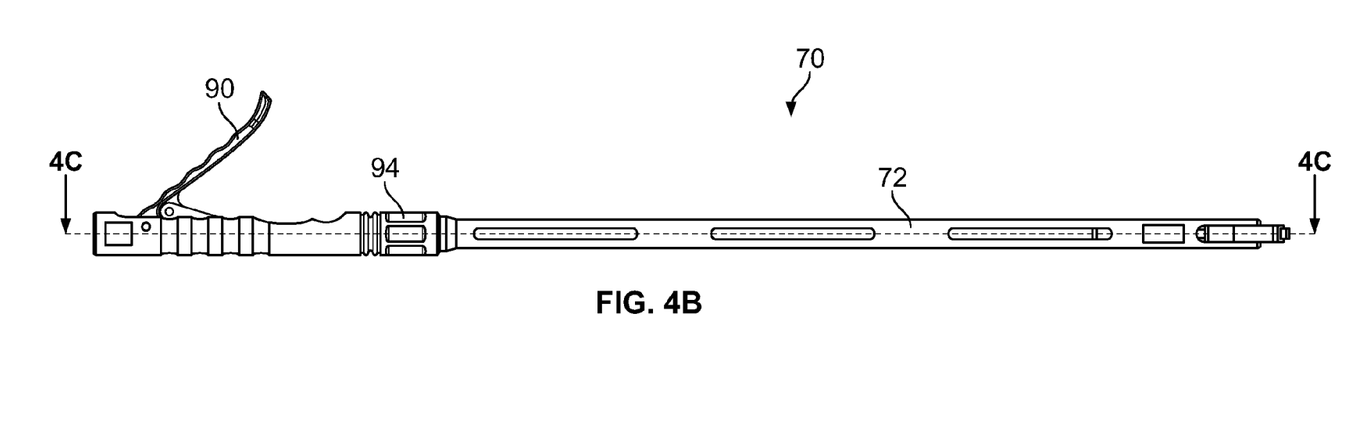
Figure 4C:
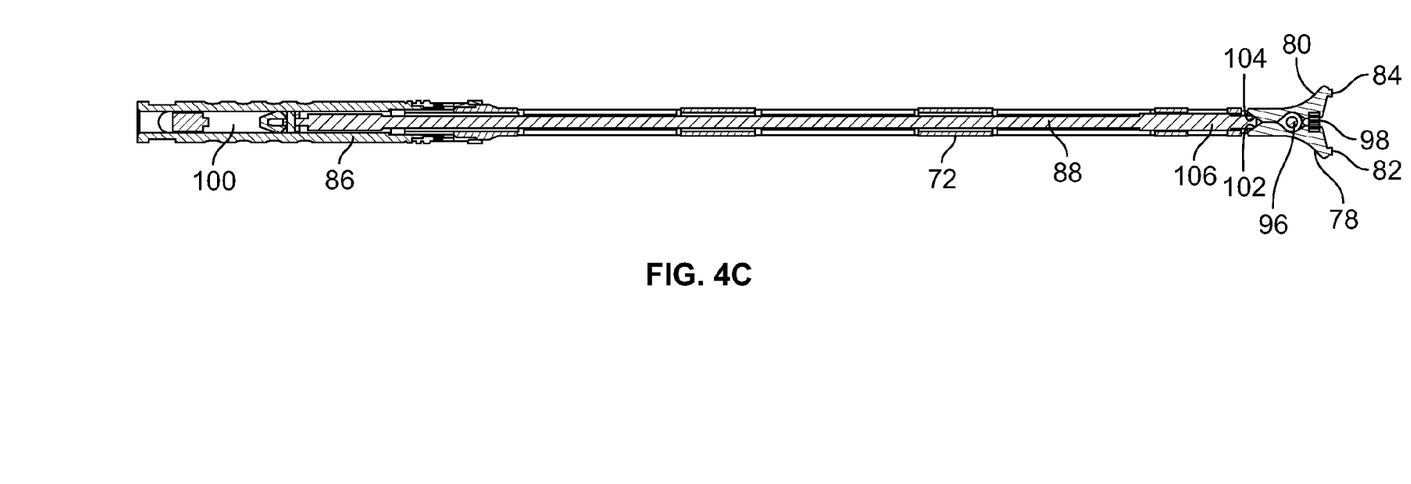
Figure 5A:
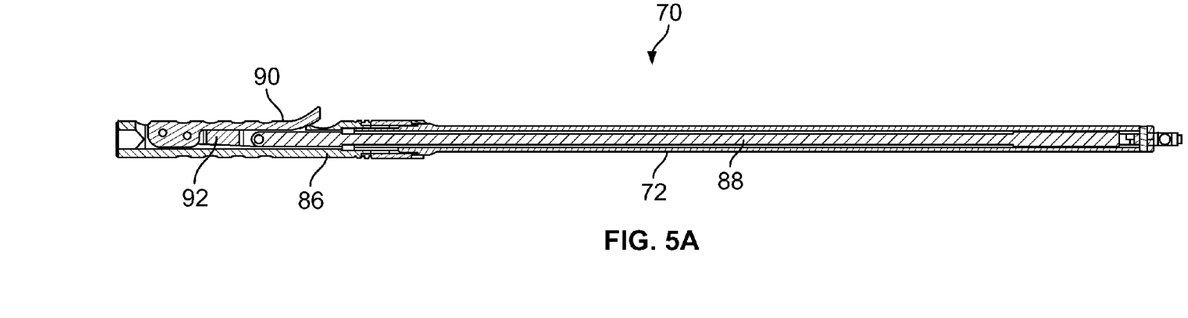
Figure 5B:
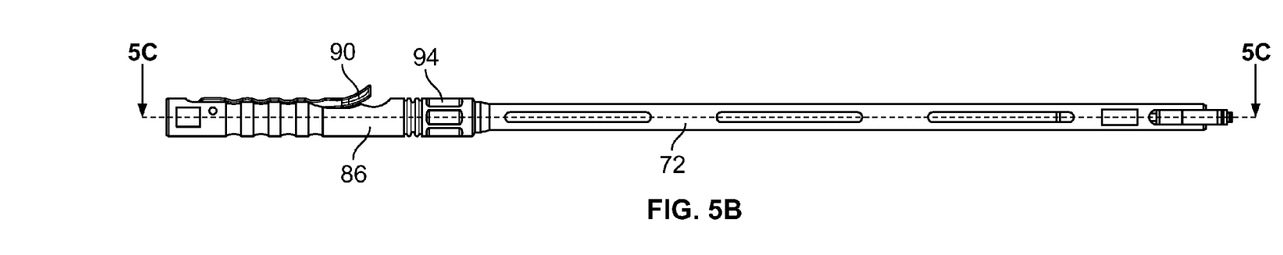
Figure 5C:
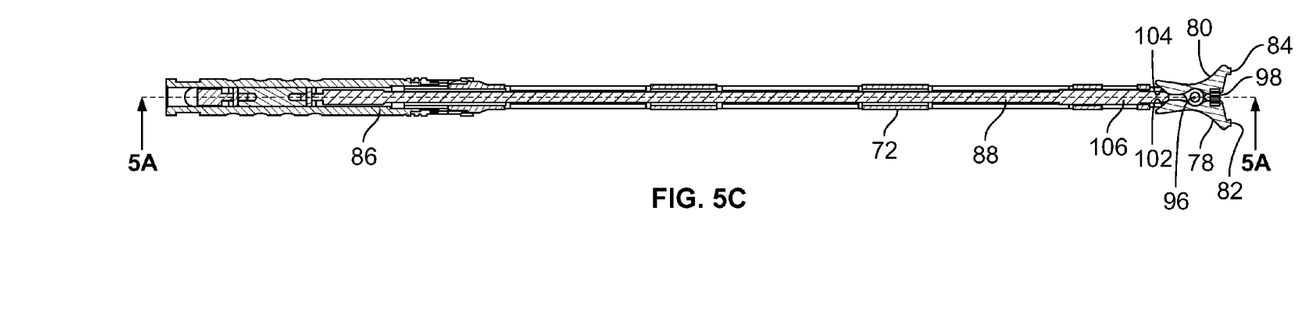
Figure 6:
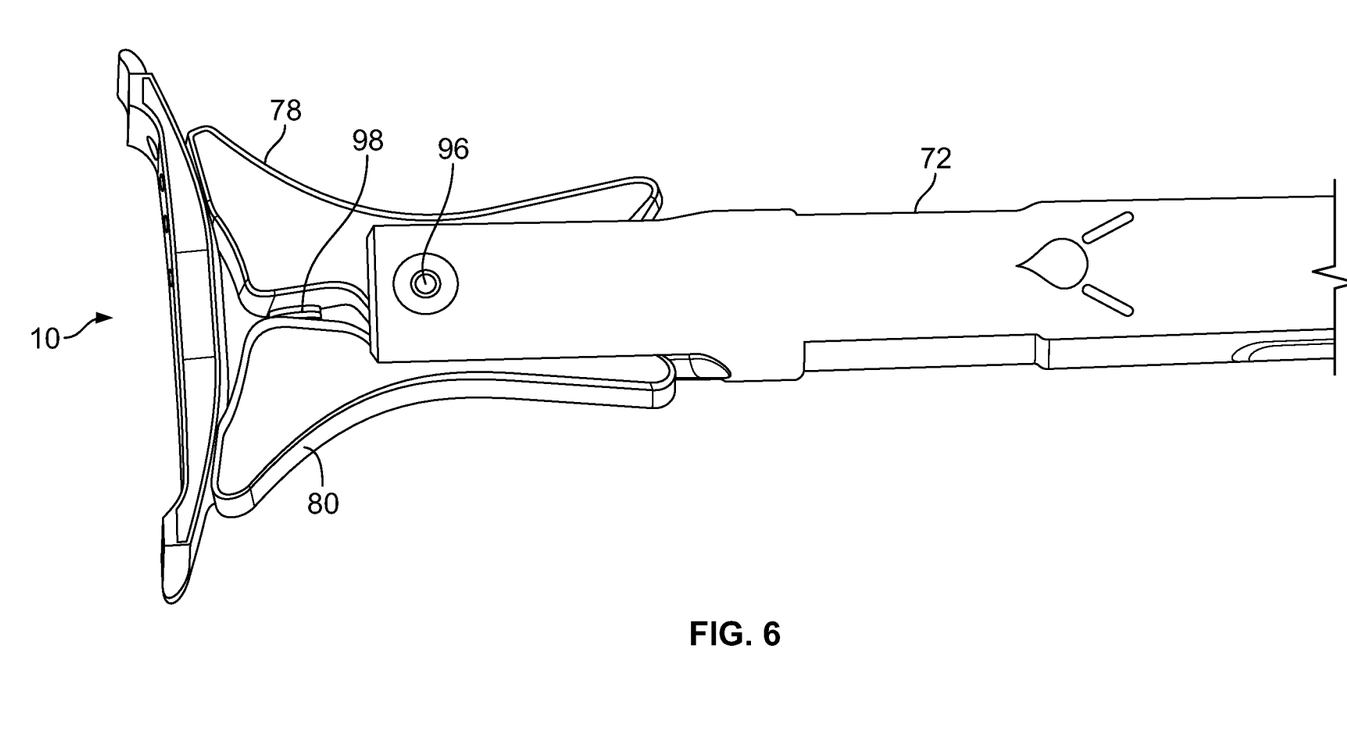

As shown in FIGS. 4B-4C and FIGS. 5A-C, inner shaft 88 may extend through opening 100 in handle 86 and hollow outer shaft 72 so as to contact tapered portions 102, 104 of arms 78, 80. In addition, a compression spring 98 may be situated between arms 78, 80 to exert a force against arms 78, 80 when moved in a particular direction (e.g., towards one another). Thus, in a resting or natural state, arms 78, 80 may be biased away from one another, as shown in FIG. 4C, thereby creating a maximum amount of distance between posts 82, 84. In contrast, as shown in FIG. 5C, arms 78, 80 and posts 82, 84 may be moved towards one another via actuation of lever 90. In particular, upon actuation of lever 90, link 92 and inner shaft 88 may be moved in a direction towards arms 78, 80 causing a distal end 106 of inner shaft 88 to contact tapered portions 102, 104 of arms 78, 80. As distal end 106 of inner shaft 88 is driven further against tapered portions 102, 104, posts 82, 84 extending from arms 78, 80 may be moved closer together against the resistive force of spring 98. Likewise, upon release of lever 90, as shown in FIG. 4B-C, link 92 and inner shaft 88 may be moved in an opposing direction away from arms 78, 80, thereby bringing arms 78, 80 back to their resting condition.

In one embodiment, adjustment nut 94 may also be utilized to change the amount that arms 78, 80 and posts 82, 84 move upon actuation of lever 90. In short, by screwing adjustment nut 94 in one direction (e.g., clockwise), outer shaft 72 and handle 86 may be moved towards or away from one another, which may affect the degree to which distal end 106 of inner shaft 88 may penetrate tapered portions 102, 104 of arms 78, 80. In this manner, the amount that posts 82, 84 are capable of moving towards or away from one another may be slightly adjusted. In one embodiment, this may be done upon manufacture, at which point adjustment nut 94 may be welded so as to preclude any further rotation and/or movement of nut 94 in the field.

During surgery, a user may utilize tool 70 to compress or deform retaining mechanism 10 and insert the same into engagement with implant 40. Specifically, after implantation of implant 40, a user may engage posts 82, 84 of tool 70 with holes 24, 26 in retaining mechanism (e.g., with lever 90 and tool 70 situated as shown in FIG. 4B-C). Then, the user may actuate lever 90 as described above to cause posts 82, 84 and arms 78, 80 to move towards one another and compress or otherwise deform retaining mechanism 10, as shown in FIG. 3C. With retaining mechanism 10 compressed or deformed, the user may manipulate tool 70 and retaining mechanism 10 to engage ledges 20, 22 extending from mechanism 10 with recesses 50, 52 in implant 40. A view of retaining mechanism 10 connected to tool 70 in a compressed or deformed state is shown in detail in FIG. 6. Next, upon release of lever 90 and arms 78, 80, retaining mechanism 10 may spring back to its uncompressed/non-deformed state causing ledges 20, 22 to engage with recesses 50, 52. A user may know that proper engagement has been made once laser marks 34 on ledges 20, 22 are no longer visible. In this manner, retaining mechanism 10 may cover one or more of fixation members 60 to prevent such from disengaging or loosening from implant 40. Tool 70 may then be removed from the surgical site and utilized for additional levels of fusion (e.g., via other implants 40), if desired.

While not discussed above, it is contemplated that suitable materials for retaining mechanism 10, implant 40, and/or fixation members 60 may be PEEK (Polyether Ether Ketone), titanium or other metals, bone material, porous metals, other biocompatible materials, or a combination of the foregoing. Such materials may also be used to construct retaining mechanism 10, implant 40, and/or fixation members 60 in a selective laser melting or porous laser sintering technique (e.g., to provide for porosity within or on such components and/or allow bone in-growth to occur on one or more surfaces of mechanism 10, implant 40, or fixation members 60).

In the devices depicted in the figures, particular structures are shown, which are adapted for use as a retaining mechanism, implant, or tool during surgery (e.g., spinal surgery). The use of alternative structures for such purposes, including structures having different lengths, shapes, and configurations is also contemplated. As an example, while cutouts 28 are shown as providing mechanically-weakened areas in retaining mechanism 10 for compression or deformation thereof, other compressible or deformable elements may be used. For instance, a retaining mechanism 10 may be comprised of a material that is compressible or deformable in and of itself, without cutouts, or a retaining mechanism 10 may be composed of a plastic or other composite material (e.g., PEEK), which has layers or regions that are compressible or deformable to permit compression or deformation of the retaining mechanism 10. Thus, so long as retaining mechanism 10 is compressible, deformable, or both to engage with implant 40, retaining mechanism 10 can adequately serve the function of preventing fixation member 60 back-out.

As yet another example, although holes 24, 26 in retaining mechanism 10 are shown as being adapted to engage with tool 70 to compress mechanism 10, other means for engaging tool 70 with retaining mechanism 10 may be provided, such as notches on mechanism 10 for engaging with posts 82, 84 of tool 70, or ledges extending from outer face 14 of retaining mechanism 10, which may engage with hooks formed on arms 78, 80 of tool 70. Indeed, the vehicle through which tool 70 engages with retaining mechanism 10 is not material, so long as tool 70 is configured to compress or otherwise deform mechanism 10 to engage mechanism 10 with implant 40.

Also, while in the figures multiple projections 16, 18 extend from retaining mechanism 10 for engaging with corresponding slots 54, 56 in implant 40, it is contemplated that one or more than two projections and corresponding slots may be provided. Likewise, the same is true of ledges 20, 22 and recesses 50, 52, in that one or more than two ledges and recesses may be provided for securing retaining mechanism 10 to implant 40. As another example, although implant 40 is shown as having multiple openings 48 for receipt of fixation members 60, it is contemplated that just one or more than three openings may be provided for one or more than three fixation members. Still further, although in the preceding disclosure multiple fixation members 60 are inserted into implant 40 and retaining mechanism 10 is utilized to cover at least a portion of such fixation members 60 to prevent back-out thereof, any number of fixation members 60 (e.g., solely one (1)) may be inserted into implant 40, and retaining mechanism 10 may be used to cover a portion of such fixation member(s) 60 to prevent back-out.

Although aspects of the invention(s) herein have been described with reference to particular embodiments, it is to be understood that these embodiments are merely illustrative of certain features of the present invention(s). It is therefore to be understood that numerous modifications may be made to the illustrative embodiments and that other arrangements may be devised without departing from the spirit and scope of the present invention(s) as defined by the appended claims.

It will also be appreciated that the various dependent claims and the features set forth therein can be combined in different ways than presented in the initial claims. It will also be appreciated that the features described in connection with individual embodiments may be shared with others of the described embodiments.

The invention claimed is:

1. A system for preventing back-out of a fixation member comprising:

a retaining mechanism including a plate having a first surface and a second opposing surface, the plate being compressible from a relaxed state in which the plate has a first maximum dimension to a compressed state in which the plate has a second maximum dimension less than the first maximum dimension; and an implant having opposed surfaces adapted to contact bone, the implant comprising an opening adapted to receive the retaining mechanism and retain it in engagement with the implant, wherein the implant has a first hole configured to receive a first fixation member and direct it into bone, and wherein when the retaining mechanism is engaged to the implant, a part of the retaining mechanism overlies the first hole and blocks the first fixation member from being inserted into the first hole of the implant and from backing out of the first hole.

2. The system of claim 1, wherein the plate includes at least one mechanically-weakened area adapted to permit compression of the plate from the first maximum dimension to the second maximum dimension.

3. The system of claim 1, wherein the retaining mechanism includes opposed ledges extending outward from sides of the plate, the ledges being adapted to engage with corresponding recesses formed in the implant, and wherein a wall partly defines each recess and overlies each ledge upon engagement of the ledges with the recesses to prevent the retaining mechanism from disengaging with the implant.

4. The system of claim 1, wherein the opening in the implant adapted to receive the retaining mechanism is bounded by opposed walls separated by a first distance, and the plate includes opposed ledges separated by a second distance, the second distance being greater than or equal to the first distance when the plate is in its relaxed state.

5. The system of claim 4, wherein the second distance is less than the first distance when the plate is in its compressed state.

6. A system for preventing back-out of a fixation member comprising:

a retaining mechanism including a plate having a first surface and a second opposing surface, the plate containing mechanically-weakened areas adapted to permit compression of the plate from a relaxed state in which the plate has a first maximum dimension to a compressed state in which the plate has a second maximum dimension less than the first maximum dimension; and an implant having opposed surfaces adapted to contact bone, the implant comprising an opening adapted to receive the retaining mechanism and retain it in engagement with the implant, wherein the implant has a first hole configured to receive a first fixation member and direct it into bone, and wherein when the retaining mechanism is engaged to the implant, a part of the retaining mechanism overlies the first hole and blocks the first fixation member from being inserted into the first hole of the implant and from backing out of the first hole.

7. The system of claim 6, wherein the retaining mechanism includes opposed ledges extending outward from sides of the plate, the ledges being adapted to engage with corresponding recesses formed in the implant, and wherein a wall partly defines each recess and overlies each ledge upon engagement of the ledges with the recesses to prevent the retaining mechanism from disengaging with the implant.

8. The system of claim 6, wherein the weakened areas include at least one cutout formed into the plate to allow the plate to compress to the second maximum dimension.

9. The system of claim 8, wherein the at least one cutout is formed entirely through the plate in a first direction extending from the first to the second surface, the cutout extending only partially through the plate in a second direction running substantially perpendicular to the first direction.

10. The system of claim 6 further comprising an insertion tool having a shaft with at least one projection, wherein the plate includes at least one hole configured to engage with the at least one projection for attaching the retaining mechanism to the implant.

11. The system of claim 6, wherein the plate includes projections extending outward from sides of the plate, the projections engaging with slots in the implant to stabilize the retaining mechanism upon engagement with the implant.

12. The system of claim 6, wherein the opening in the implant adapted to receive the retaining mechanism is bounded by opposed walls separated by a first distance, and the plate includes opposed ledges separated by a second distance, the second distance being greater than or equal to the first distance when the plate is in its relaxed state.

13. The system of claim 12, wherein the second distance is less than the first distance when the plate is in its compressed state.

* * * * *